United States Patent [19]
Hagele

[11] Patent Number: 6,041,978
[45] Date of Patent: Mar. 28, 2000

[54] LIQUID DROPPER FOR UPRIGHT EYE DROP INSTILLATION

[76] Inventor: James Hagele, 13262 Evergreen Dr., Nevada City, Calif. 95959

[21] Appl. No.: 09/183,927

[22] Filed: Oct. 30, 1998

[51] Int. Cl.[7] .................................................. B65D 47/18
[52] U.S. Cl. ........................ 222/420; 222/211; 604/294; 604/295; 604/296
[58] Field of Search ..................... 222/211, 420; 604/294, 295, 296, 297, 298, 299, 301, 302

[56] References Cited

U.S. PATENT DOCUMENTS

| | | | |
|---|---|---|---|
| 2,728,491 | 12/1955 | Aneshansley | 222/211 X |
| 2,783,919 | 3/1957 | Ansell | 222/211 |
| 3,756,478 | 9/1973 | Podell et al. | 222/211 X |

FOREIGN PATENT DOCUMENTS

| | | | |
|---|---|---|---|
| 453235 | 12/1948 | Canada | 222/211 |

*Primary Examiner*—Kevin Shaver
*Assistant Examiner*—Thach Bui
*Attorney, Agent, or Firm*—Heisler & Associates

[57] ABSTRACT

A dropper 10 is provided which allows a person to precisely instill eye drop solution while the person's head and the dropper 10 are oriented in an upright position. The dropper 10 includes a deformable, resilient reservoir 40 of medicinal fluid which may be squeezed to to cause the fluid to flow up a supply conduit 15 to a housing 20 of the dropper 10. The fluid then flows out an opening 32 in a tip 31 of the dropper 10. An inner rod 130 or inner delivery tube 30 extends along an interior of the supply conduit 15. The tube 30 or rod 130 discourages air bubbles from being entrapped within the conduit 15. The tip 31 extends forward from a center line 41 along an extension 27 which is substantially perpendicular to a collar 50 extending up from the reservoir 40.

9 Claims, 4 Drawing Sheets

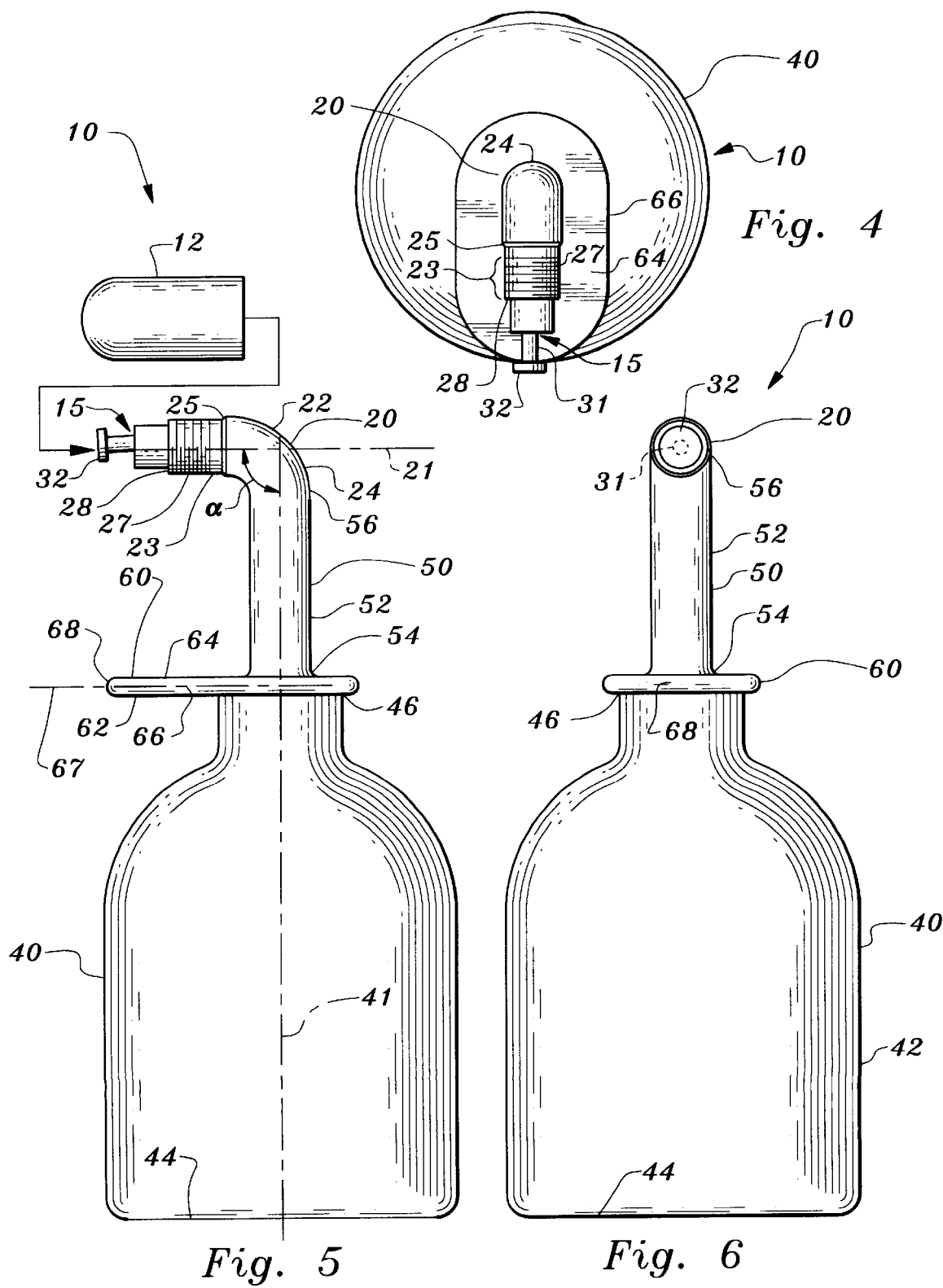

LIQUID DROPPER FOR UPRIGHT EYE DROP INSTILLATION

FIELD OF THE INVENTION

This invention relates to droppers for dispensing liquids. More particularly, this invention relates to droppers for instilling medicinal liquids, i.e., eye drops, in a person's eye while both the person's head and the dropper are oriented in a substantially upright position. It may also be used, however, in the conventional way of instilling drops into the eye where the head is tilted back and the bottle is held above.

BACKGROUND OF THE INVENTION

Self-administration of medicinal eye drops tends to be both annoying and awkward. Typically, a person's head must first be tilted backward until the person is looking straight above. This creates a maximal target area of the person's eye and tends to help retain the falling eye drop into the person's eye. Then, while maintaining the person's head in this extended position, the person must invert a conventional eye dropper bottle over the eye and simultaneously attempt to precisely position the tip of the dropper directly over the target eye area while holding their eyelids open with the other hand. Once properly positioned, the person must then squeeze the reservoir of the dropper bottle to dispense the medicinal liquid, without moving either their head or the dropper.

Several factors complicate this conventional eye drop installation procedure. First, it is physically difficult for many persons, particularly when self-administering the eye drops, to both position and maintain their heads in a tilted back orientation. Second, many persons have difficulty raising their arms up over their heads due to limitation of motion of the wrist or shoulder, thus making it difficult for such persons to accurately position a conventional eye dropper bottle over the targeted eye area. Third, there are some individuals who may get vertigo or dizziness when placing their head in a backward position while instilling drops into their eyes.

One logical solution to the difficulty of raising a dropper bottle over the person's head is to configure the eye dropper bottle in an upright manner with a tip having an opening for release of drops located above a reservoir. One such prior art eye dropper bottle is described in the patent to Podell (U.S. Pat. No. 3,756,478). Some bottles deliver fluid in such an upright manner by utilizing a tube that extends from the reservoir where the liquid is stored to an outlet above. Such an upright orientation has many problems, however. First, small pockets of air are trapped between drops of liquid within the tube of such a conventional upright dropper, and when the reservoir of the dropper is squeezed, a mixture of air and medicinal liquid will result. The air/liquid droplet often will not release from the tip of the dropper in a consistent fashion. Also, the air to liquid proportions of the droplet vary so widely that it is not accurately quantifiable, so the person is not able to determine if the drop was enough of a dosage or if further doses are needed.

Also, if the tip of the dropper bottle is not held in a substantially inverted position with the tip directed downward, an eye drop may adhere along the exterior of the tip away from the opening of the tip. Hence, the drop will be released at a point spaced away from the opening of the tip of the dropper and tend to miss the person's eye altogether. Often a drop will adhere to the tip of the dropper and will not release until a second drop is expressed from the bottle. This causes considerable waste as the drop(s) or a portion of them never release from the tip.

All of the above factors further amplify the difficulty of self-administering an eye drop. Hence, a person may be substantially impeded from accurately and reliably self-administering an eye drop solution.

Due to the inherent inaccuracy associated with the conventional process of instilling eye drops, a person may instill either more or less than the prescribed dosage. For example, recognizing that a portion of the intended dosage has missed its target, a person may elect to administer a substantially increased dosage based upon his subjective assessment of the portion of each droplet that actually reached or missed its intended target area. If too much medicinal liquid is instilled, the overdose could prove detrimental to the person. Additionally, overdosing and waste from inaccuracy may cause the prescription volume to be prematurely consumed, thereby shortening the duration of the treatment and potentially failing to adequately treat the condition for which the medicine was intended. It also greatly adds to the expense of treating ocular conditions, especially chronic situations such as glaucoma. Correspondingly, if the person fails to instill the required dosage in his eye, the treatment may be inadequate.

The prior art is replete with numerous attempts to provide devices to more easily instill medicinal liquids in a person's eye. The bulk of the attempted methods still require that the head be tilted back while simultaneously dispensing the liquid eye medicine. Various devices described in the prior art incorporate eye cups which are placed fully over at least one eye before dispensing the medicinal liquid. These devices are configured to wash the eye, rather than deliver drops of medication.

Today, standard dropper bottles consist of a small deformable reservoir and a conically-shaped tip. These standard dropper bottles must be inverted over a person's eye during use. Many manufacturers market both over-the-counter and prescription eye drop solutions which are dispensed from these conventional eye dropper bottles.

A variation of standard dropper bottles is described by Menchel et al. in U.S. Pat. No. 5,069,675. The Menchel patent discloses an applicator for liquid eye preparations which includes a resilient container and associated head similar to those described above. The Menchel dropper bottle differs only in that a different type of cap is placed over the head of the dropper. Menchel's cap includes a laterally protruding spout which is rested against a person's lower eyelid while the person self-administers the medicinal liquid into his eye. However, Menchel's dropper must also still be inverted, with the reservoir of medicinal liquid positioned above the spout, to allow instillation of the eye drops. Further, placing the tip of the laterally protruding spout of Menchel's invention immediately adjacent the surface of the eye creates a potentially hazardous circumstance. Any inadvertent movement could cause the tip to jab the person's eye, causing some damage or at least, temporary irritation. Additionally, resting the laterally protruding spout against a person's lower eyelid could contaminate the spout and the remaining medicinal solution contained within the reservoir of the dropper.

Accordingly, a need exists for a dropper for medicinal eye liquid which can be used with the dropper in an upright position, having its reservoir of medicinal liquid positioned below its tip, and a person's head also oriented in an upright position. A corresponding need exists for such an eye dropper where no portion of the dropper tip touches a person's eyes or eyelids while being administered. A further corresponding need exists for such an eye dropper where the tip of the dropper can be easily and precisely positioned by a person over his eye to maximize accuracy during instillation of the eye drops. This can be accomplished best by the use of a mirror where both the eye and the tip of the bottle are well visualized. Finally, a need exists for such an eye dropper capable of discharging eye drops of substantially equivalent volume to ensure accurate dosage of the medicinal liquid is administered to a patient's eye.

SUMMARY OF THE INVENTION

The present invention is designed so that an individual can instill the eye drops without extending his/her head or elevating the bottle above the head. It is best accomplished with the use of a mirror. Mirrors are readily available in the home, in the car, at work and even carried by some individuals. By using a mirror, better placement can be obtained and also greater protection is afforded from inadvertently touching any eye structures, especially the cornea. Also, it will prevent touching the eyelids with the tip and contaminating the eye drops in the bottle. If the drop is accurately placed in the eye, there is much less waste and also greater medicinal benefits. Because of the design of the bottle, it does not need to be inverted when instilling eye drops into the eye. Rather, the bottle which is grasped and held by the fingers in an upright position can at all times be seen in the mirror and its approximation to the eye is not obscured by the bottle itself. Thus the tip of the bottle is visible and easily directed to its intended position.

The dropper of the present invention includes a resilient squeezable reservoir for storing a medicinal solution. A supply conduit provides a means to transfer the medicinal solution from the reservoir to a tip of the dropper without inverting the reservoir of the dropper over the dropper tip, i.e., maintaining the bottle in an upright position. The supply conduit can be configured as a hollow tube or can include an outer cylindrical casing which enshrouds either a second smaller diameter hollow delivery tube or a solid rod. The outer casing, in tandem with the hollow delivery tube or solid rod, forms a liquid pathway configured as an elongate cylindrical annulus.

In a most preferred embodiment of the present invention, where a solid elongate cylindrical rod is surrounded by the outer casing, medicinal liquid flows only through the elongate annulus. In a preferred embodiment of the present invention, where the outer casing enshrouds a second smaller diameter hollow delivery tube, medicinal liquid flows through both the delivery tube and the elongate annulus. Providing the supply conduit with an elongate annulus configuration helps prevent air pockets from being trapped within the fluid column within the supply conduit.

The supply conduit is preferably slightly bent near its midsection so that its inlet will be located at the lowest point of the reservoir of the dropper. The dropper is tilted slightly forward during use, hence, the lowest point of the reservoir is at the lower forward corner of the reservoir. Locating the inlet of the supply conduit adjacent this lower forward corner ensures that substantially all the medicinal solution within the reservoir will be used, even though the dropper is not inverted when drops are dispensed. The tip of the conduit and the inlet of the supply conduit are preferably designed to face the same direction.

During use according to a preferred configuration of the invention, the index finger is used to retract the outer margin of the lower eyelid away from the eye, thus creating a small pocket into which the drop is instilled. The tip of the bottle is then placed slightly above the created pocket of the lower eyelid. Using a mirror both the eyelid and the tip of the bottle can be well visualized and placement guaranteed. Once the dropper has been properly positioned, the side walls of the reservoir are manually squeezed to displace the medicinal solution up the supply conduit and out the tip of the dropper. Fluid movement of the delivery tube or solid rod within the outer casing of either embodiment causes sufficient physical disturbance to ensure any inadvertently trapped air pockets are dislodged to prevent a mixture of air and medicinal liquid during instillation.

The bottle is designed with a positioning notch in its upper portion and this area is placed over the tip of the finger that is retracting the eyelid. This permits better placement and also protects from touching eye structures. If another individual, such as a spouse or an assistant, is instilling drops into the patient's eye, the finger beneath the positioning notch of the bottle prevents the patient from unexpectedly moving forward into the tip of the bottle and being harmed. The forward movement of the patient will only result in pushing the hand of the assistant and the bottle away from the eye.

Where the most preferred embodiment of dropper of the present invention includes a supply conduit having an elongate solid rod enshrouded within the outer casing, medicinal liquid will be discharged from the outlet of the supply conduit's elongate annulus. This particular configuration of the present invention also preferably includes a smooth, round ball at the tip of the rod. The ball provides a preferential low point at the tip of the supply conduit which will tend to cause droplets of medicinal liquid to form on and release from the underbelly of the ball. The smooth, round ball also provides additional safety should it inadvertently touch the person's eye.

There may be circumstances where the patient or an assistant desires to use the present invention bottle in the conventional way of extending the head back and elevating the bottle above the head while dropping the drop from above. This is especially true when the patient does not have access to a mirror to visualize the eye while instilling the eye drop. The design of the invention bottle also permits this method of instilling drops into the eye and is easier to use than the present bottles available today. The bottle is grasped with the fingers and the horizontal tip of the dropper is turned toward the eye and held above the eye while simply releasing the drop from above. There is no need to elevate the bottle in a fully vertical manner. Rather, the bottle can be held in a nearly horizontal manner while instilling the drop. This makes it much easier on the elevation of the arm and the shoulder and the backward extension of the head of the patient. It is the versatility of the current invention dropper that makes it so desirable.

OBJECTS OF THE INVENTION

A primary object of the present invention is to provide an eye dropper which allows a person's head to be oriented in a normal upright position while eye drops are instilled.

Another object of the present invention is to provide an eye dropper that can accurately target the tip of the dropper over the eye to allow precise eye drop instillation.

Another object of the present invention is to provide an eye dropper configured to prevent inadvertent movement of the dropper and its tip, thereby preventing accidental injury to the tissues of the eye.

Another object of the present invention is to provide a dropper which maximizes utilization of the medicinal liquid within the reservoir and avoids waste.

Another object of the present invention is to provide an eye dropper that may be used without being raised over a person's head.

Another object of the present invention is to provide an eye dropper to consistently and reliably accurately target the tip of the eye dropper over the eye to minimize the number of dispensed eye drops which do not land on the intended target area of the eye.

Another object of the present invention is to provide an eye dropper which discourages entrapment of air bubbles in a supply conduit so that bubbling at an outlet of the dropper is avoided and drops of consistent size are dispensed.

Another object of the present invention is to provide an eye dropper bottle which can either be used in an upright fashion or in a conventional tilted fashion.

Other further objects of the present invention will become apparent from a careful reading of the included drawing figures, the claims and detailed description of the invention.

BRIEF DESCRIPTION OF THE DRAWINGS

FIG. 4 is a top plan view of the preferred embodiment of the dropper of the present invention.

FIG. 5 is a side elevation view of the preferred embodiment of the dropper of the present invention.

FIG. 6 is a front elevation view of the preferred embodiment of the dropper of the present invention.

DESCRIPTION OF THE PREFERRED EMBODIMENT

Figure 1:
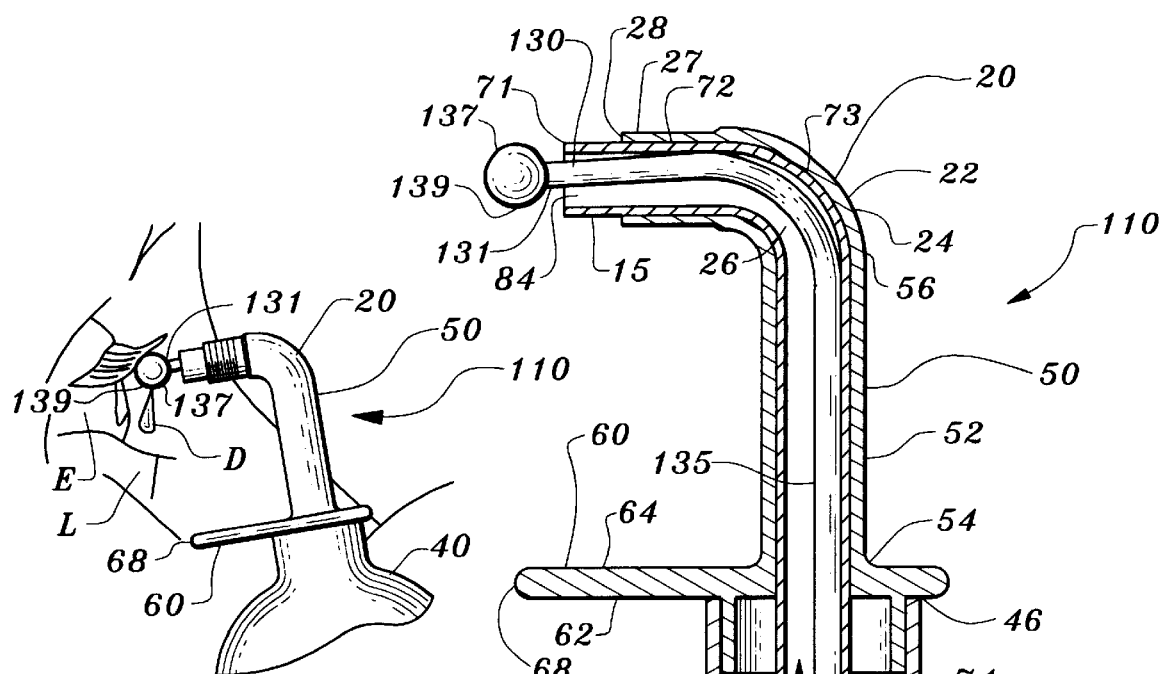
FIG. 1 is a side elevation view of an upper end of a most preferred embodiment of the dropper of the present invention in use with a drop of liquid about to release from the underbelly of a ball at a tip of the dropper and into a person's eye.

Referring to the drawings wherein like reference numerals represent like parts throughout the various drawing figures, reference numeral 10 (FIG. 3) is directed to a dropper for instilling liquids in a person's eye E while both the dropper 10 and the person's head are oriented in an upright position. The dropper 10 is oriented in a substantially upright position when its liquid reservoir 40 is lower than an opening 32 through which droplets D (FIG. 1) of medicinal liquid are dispensed.

Figure 3:
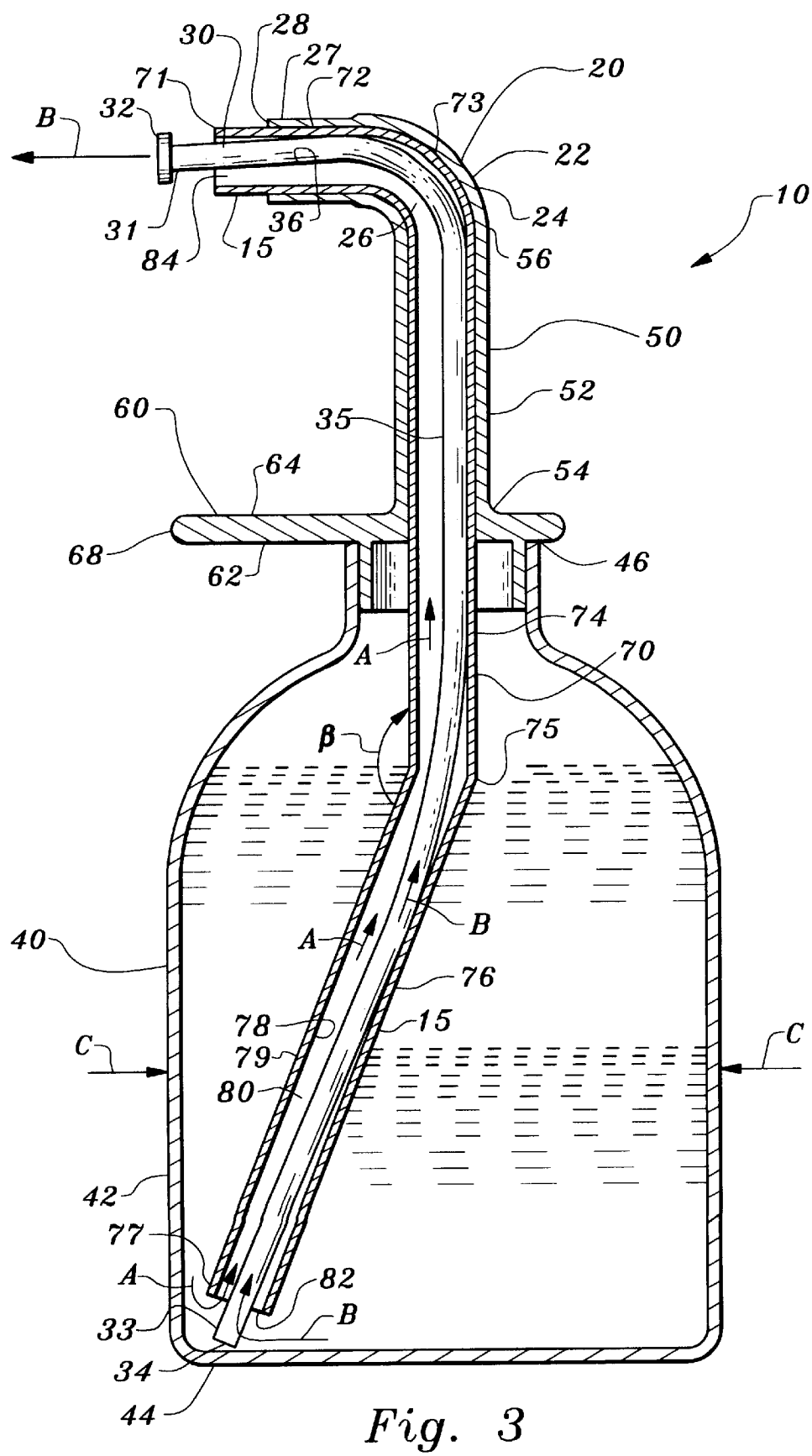
FIG. 3 is a side cross-sectional elevation view of the preferred embodiment of the dropper of the present invention.

In essence, and with particular reference to FIG. 3, the basic details of a preferred embodiment of the dropper 10 are described. A supply conduit 15 provides a passageway for medicinal liquid to flow from a reservoir 40 of the dropper 10. The supply conduit 15 includes a slender delivery tube 30 enshrouded by a larger outer casing 70. An external housing 20 atop the reservoir 40 supports the supply conduit 15 above the reservoir 40. A preferably cylindrical collar 50 joins the housing 20 to the reservoir 40 and frictionally engages the outer casing 70 of the supply conduit 15. A protective shoulder 60 is interposed between the collar 50 and the reservoir 40. An irregular hollow elongate annulus 80 for liquid flow is formed by the insertion of the delivery tube 30 within the outer casing 70.

More specifically, and with particular initial reference to FIGS. 3 and 4, details of the preferred embodiment of the dropper 10 of the present invention are described. The dropper 10 of the present invention includes a deformable reservoir 40 having a vertical center line 41 oriented preferably substantially perpendicular to a central axis 21 of an extension 27 at an upper end of the housing 20 at an angle α (FIG. 5).

The reservoir 40 of the dropper 10 includes a preferably cylindrical side wall 42 which extends and merges with a circular base 44 to form the floor of the reservoir 40. A circular upper end 46 of the reservoir 40 opposite the base 44 forms an open end of the reservoir 40 (FIG. 3). The sidewall 42 is preferably formed of sufficiently soft plastic to allow the side wall 42 to be squeezed inward somewhat.

Figures 7, 8, 9:
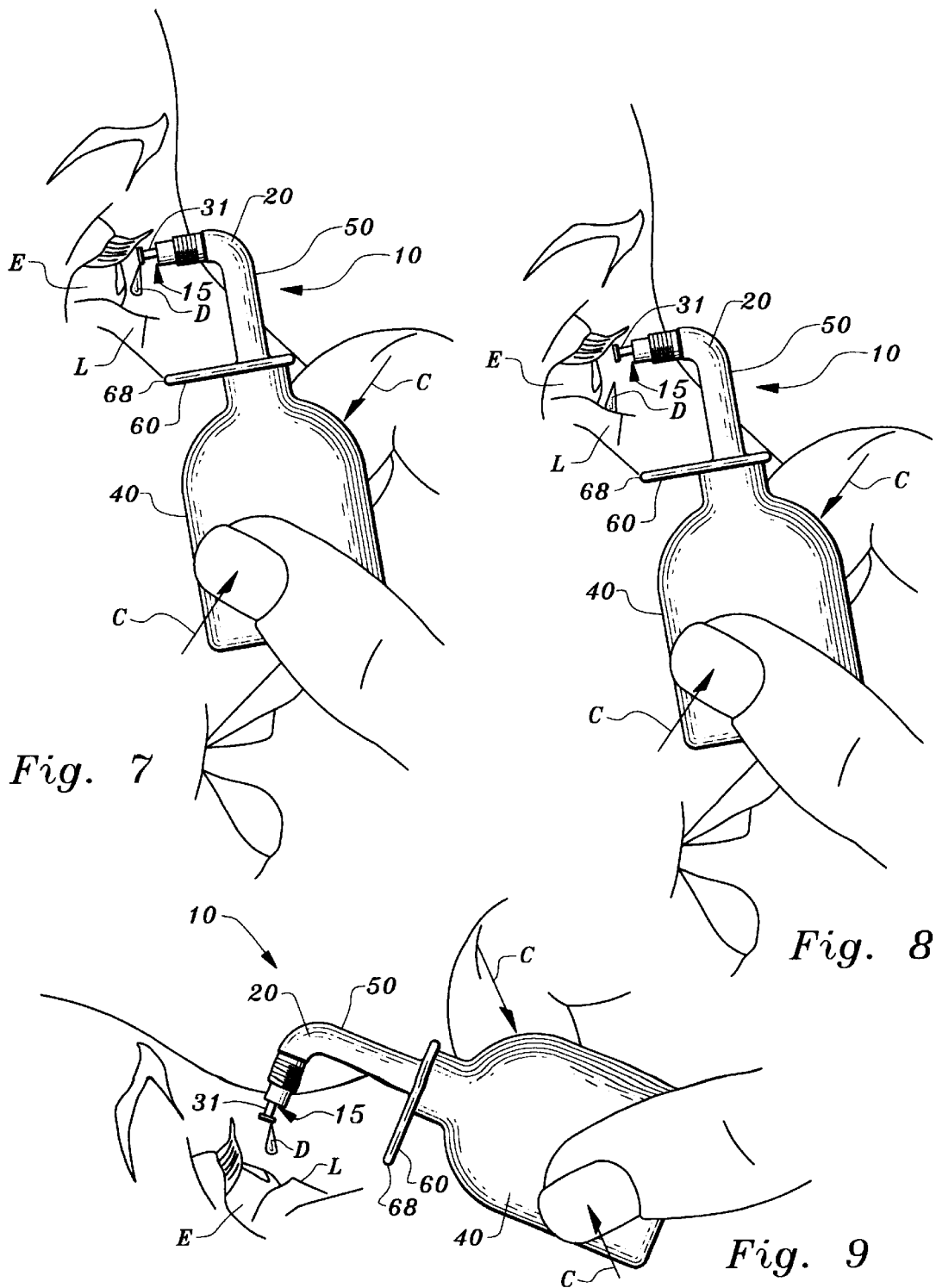
FIG. 7 is a side elevation view of the preferred embodiment of the dropper of the present invention in use with a drop about to release from the tip of the dropper.
FIG. 8 is a side elevation view of the preferred embodiment of the dropper of the present invention in use with a drop of liquid having been released from the tip of the dropper and entering a pocket formed between a person's eye and a lower eyelid.
FIG. 9 is a side elevation view of the preferred embodiment of the dropper of the present invention in use with a drop of liquid being released from the tip of the dropper in the conventional way where the head of the person is tilted back and the bottle is elevated above the head.

A mateable collar 50 releasably couples with the upper end 46 of the cylindrical side wall 42 of the reservoir 40. The collar 50 includes an elongate cylindrical surface 52 which extends from a point adjacent the upper end 46 of the reservoir 40 to join a lower portion of the housing 20 of the dropper 10 to the reservoir 40. A bottom edge 54 of the collar 50 is located at a lower end of the cylindrical surface 52 adjacent the upper end 46 of the reservoir 40. An opposing top portion 56 of the collar 50 is located adjacent a lower portion of the housing 20 of the dropper 10. The collar 50 is sized to slidably receive and retain the outer casing 70 of the supply conduit 15 within its cylindrical surface 52. The cylindrical surface 52 of the collar 50 has sufficient height to accurately position the tip 31 of the dropper 10 over a person's eye E for accurate eye drop instillation when the dropper 10 is placed in position against the person's cheek prior to use (FIG. 7).

A shoulder 60 extends laterally from and surrounds the bottom edge 54 of the cylindrical surface 52 of the collar 50 (FIG. 3). The shoulder 60 includes a planar lower surface 62 opposite a parallel planar upper surface 64. When the collar 50 is coupled with the reservoir 40, the planar lower surface 62 of the shoulder 60 abuts the upper edge 46 of the reservoir 40. The shoulder 60 is oblong having an oval perimeter 66 (FIG. 5). A major axis 67 of the oval perimeter 66 is preferably parallel to the central axis 21 of the housing extension 27. An apogee 68 at a distal end of the oval perimeter 66 of the shoulder 60 is located a distance from the centerline 41 of the reservoir 40 which coincides with the outer radius of the cylindrical side wall 42 of the reservoir 40 of the dropper 10 (FIG. 3) and the radial perpendicular distance of the tip 31 from the centerline 41 of the reservoir 40.

The shoulder 60 of the dropper 10 serves several purposes. First, it prevents inadvertent impact of the tip 31 of the dropper 10 on a person's eye E while the person instills the medicinal solution. Second, the shoulder 60 ensures that the tip 31 of the dropper 10 is correctly positioned directly above the person's eye E and the receptive well formed in the lower eyelid L. Additionally, the shoulder 60 serves to minimize potential reflexive blinking by securely retracting the lower eyelid L while instilling the medicinal solution.

The dropper 10 further includes the elongate housing 20 (FIG. 3) extending up from the collar 50 which frictionally engages and supports the supply conduit 15. The housing 20 has a generally elongate cylindrical shape and is preferably made from a deformable and resilient thermoplastic material which is capable of being used in an injection molding process. The housing 20 and collar 50 are extensions of each other with no clear transition from one to the other. The housing 20 bends to cause the extension 27 to align the central axis 21, is hollow, with an interior cavity 26 and an outer surface 22. The interior angle α formed between the central axis 21 of the extension 27 and the center line 41 of the reservoir 40 is shown as approximately 90° but may be modified somewhat to accommodate varying reservoir 40 shapes. Hence, the dropper 10 of the present invention could be manufactured so that the interior angle α is as low as 60° and as high as 120°.

At one end, the outer surface 22 of the housing 20 includes the extension 27 with a threaded portion 23 to threadably receive a sealing cap 12 (FIG. 5). The cap 12 covers the tip 31 while the dropper 10 is not in use to prevent undesired liquid leakage and contamination of the tip 31 by environmental particulates. At an end opposite the threaded portion 23, the outer surface 22 forms a rear surface 24. A radially reducing taper portion 25 extends from the outer surface 22 of the housing 20 in a direction away from the rear surface 24 to join the cylindrical extension 27 to the outer surface 22. The extension 27 terminates at a planar annular fore end 28, which is furthest from the centerline 41 of the reservoir 40. The extension 27 has a smaller diameter than the outer surface 22 and the threaded portion 23 of the housing 20 to allow the cap 12 to be threaded onto the threaded portion 23 and form a sealing connection with the taper portion 25.

With reference to FIG. 3, the supply conduit 15 is frictionally engaged within the cavity 26 of the housing 20. The supply conduit 15 includes a larger, preferably cylindrical, outer casing 70 which substantially enshrouds a slender elongate hollow delivery tube 30. The outer casing 70 of the supply conduit 15 extends from a nose 71 to terminate at a shoe 77 positioned adjacent the base 44 of the reservoir 40.

In a most preferred embodiment of the dropper 110 (FIG. 2), the shoe 77 has a frustoconical shape to create a taper which allows the shoe 77 of the casing 70 to come closer to the lower forward corner of the reservoir 40 to maximize consumption of liquid stored within the reservoir 40. In a preferred embodiment of the dropper 10 (FIG. 3), the shoe 77 is preferably cylindrical. The reservoir 40 will still be substantially drained in this preferred embodiment of the dropper 10 since the hollow delivery tube 30 has a smaller radius than that of the outer casing 70, and hence, can come equally close to the lower forward corner of the reservoir 40.

A lateral leg 72 of the outer casing 70 extends from the nose end 71 through the interior cavity 26 of the housing 20. The lateral leg 72 of the outer casing 70 forms a preferably right angle top bend 73 with a substantially vertical upper leg 74 of the casing 70 within the cavity 26 adjacent the rear surface 24 of the housing 20. The substantially vertical upper leg 74 of the outer casing 70 extends downward from the top bend 73 along the vertical center line 41 of the reservoir 40. The upper leg 74 forms an elbow bend 75 within the upper portion of the reservoir 40 having an angle β with a lower leg 76 of the outer casing 70 (FIG. 3). The angle β of the elbow bend 75 in the outer casing 70 is sufficient to locate the shoe 77 of the lower leg 76 of the outer casing 70 adjacent the base 44 of the reservoir 40 nearest the cylindrical side wall 42 of the reservoir 40 on a forward portion of the reservoir 40 beneath the orifice 32 of the tip 31 of the delivery tube 30. The tip 31 is provided with a blunted annular bumper surrounding the orifice 32 to minimize danger of injury to the eye E should the tip 31 inadvertently contact the eye. The elbow bend 75 ensures that the shoe 77 of the outer casing 70 remains immersed in liquid until substantially all the liquid has been displaced from the reservoir 40. The casing 70 includes an exterior cylindrical surface 79 which is frictionally engaged by the housing 20 and collar 50. An opposing interior cylindrical surface 78 of the casing 70 is adjacent the liquid and touches the hollow delivery tube 30 at various locations along the length of the casing.

With further reference to FIG. 3 the hollow delivery tube 30, preferably of slightly greater length than the outer casing 70, is positioned within the outer casing 70 such that a tip 31 and an opposing tail 33 of the delivery tube 30 are spaced approximately equidistant from the nose 71 and shoe 77, respectively, of the outer casing 70. The delivery tube 30 is preferably made of a resilient thermoplastic material. The delivery tube 30 is preferably initially formed as a straight length of cylindrical tubing. The slender delivery tube 30 acts as a fluid conduit to transport medicinal liquid from the reservoir 40 to the tip 31 of the dropper 10. Fluid flows through an intake 34 in the tail 33 of the delivery tube 30 to exit out an orifice 32 in the tip 31 of the delivery tube 30. The orifice 32 in the tip 31 is preferably located a distance away from the center line 41 of the reservoir 40 the same as the distance which the side walls 42 of the reservoir 40 are located away from the center line 41 of the reservoir 40. When placed in an upright position, the tip 31 of the dropper 10 is substantially vertically aligned with the side walls 42 of the reservoir 40.

The delivery tube 30 has a preferably cylindrical elongate exterior wall 35. The exterior wall 35 of the delivery tube 30 rests adjacent and is frictionally engaged by the interior surface 78 of the outer casing 70 at various locations along the casing 70. By slidably inserting the delivery tube 30 within the outer casing 70, the natural resiliency of the delivery tube 30 will cause the exterior wall 35 to impinge upon the interior surface 78 of the outer casing 70 at various points along the length of the outer casing 70 adjacent regions where the outer casing 70 is bent. Engagement points include the area adjacent the elbow bend 75 and top bend 73 of the outer casing 70. The material of the delivery tube 30 should have sufficient flexibility to be slidably engaged within the outer casing 70, during assembly, but sufficient resiliency to prevent the delivery tube 30 from being easily withdrawn from the outer casing 70.

An elongate fluid annulus 80 is formed by the insertion of the delivery tube 30 into the outer casing 70. The annulus 80 has a fluid volume determined by the inner diameter of the outer casing 70 less the outer diameter of the delivery tube 30. The fluid volume of the annulus 80 is preferably substantially greater than the fluid volume of the delivery tube 30. The annulus 80 includes an annular entry 82 defined by the shoe 77 of the outer casing 70 and the exterior wall 35 of the delivery tube 30. An opposing annular outlet 84 is located nearest the fore end 28 of the housing 20 and is defined by the nose 71 of the outer casing 70 and the exterior wall 35 of of the delivery tube 30. The fluid annulus 80 has a somewhat irregular cross-section along its length due to the manner in which the resilient delivery tube 30 frictionally engages the inner surface 78 of the outer casing 70 at various points along its length. The delivery tube 30 is preferably decentralized within the outer casing 70. Decentralization, creating irregular cross-sections along the length of the annulus 80, minimizes the probability that fluid surface tension and capillary attraction will create blankets of fluid within the annulus 80 which would tend to trap air between columns of fluid within the annulus 80.

The fluid annulus 80 provides a pathway for liquids which tends to not allow air bubbles to become trapped therein. Hence, a steady stream of liquid is dispensed at the tip 31, rather than occasional sputtering of liquid when air pockets are discharged.

Figure 2:
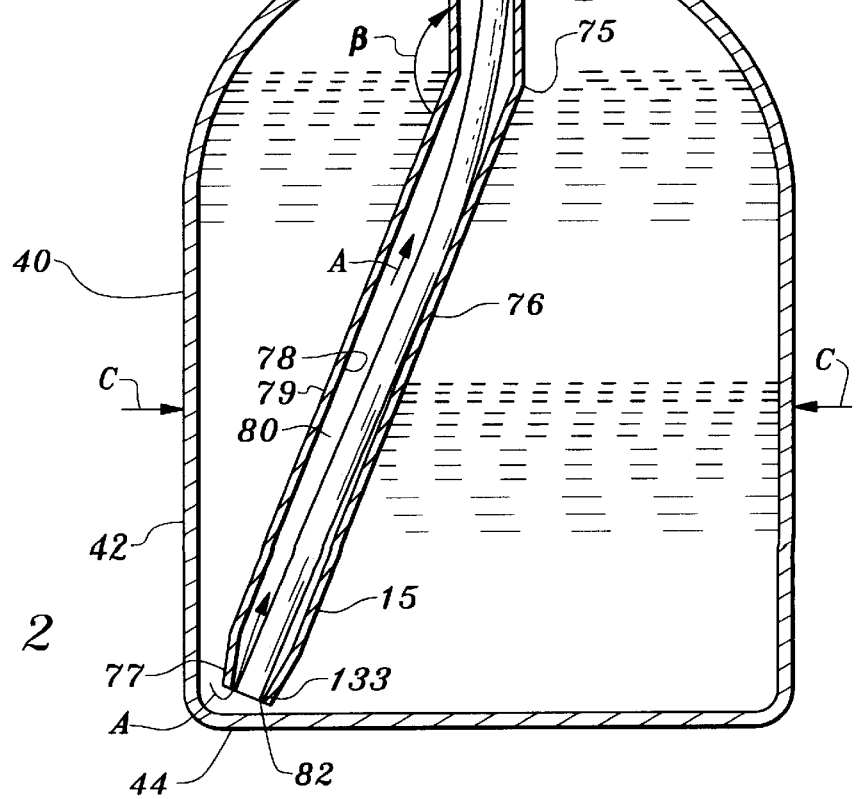
FIG. 2 is a side cross-sectional elevation view of the most preferred embodiment of the dropper of the present invention.

With reference to FIGS. 1 and 2, in a most preferred embodiment of the dropper 110 of the present invention, a solid elongate rod 130, rather than a hollow delivery tube 30, is slidably inserted within the outer casing 70 of the supply conduit 15. Hence, in this most preferred embodiment 110, the annulus 80 is the sole fluid pathway through which fluid flows from the reservoir 40 to an outlet 84 of the annulus 80 for discharge toward a person's eye E. The elongate rod 130 extends from an end 133 adjacent the shoe 77 of the outer casing 70 to terminate at an opposing tip 131 adjacent the nose 71 of the outer casing 70. The tip 131 of the rod 130 extends slightly past the nose 71 of the outer casing 70 so that drops D of medicinal liquid falling from the tip 131 of the rod 130 will not contact the nose 71 of the outer casing 70 as they fall toward a person's eye E.

A round, smooth ball 137 is attached to the tip 131 of the rod 130 to act as a primary point of droplet D formation and departure. The ball 137 has an underbelly 139 which is naturally lower than an exterior wall 135 of the rod 130 where the ball 137 is joined to the tip 131 of the rod 130. The ball 137 has a diameter preferably approximately two to three times that of the rod 130. The ball 137 is centered on the tip 131 so that the underbelly 139 of the ball 137 is located lower than the lowest point of the exterior wall 135 of the rod 130 at the tip 131, when the dropper 110 is in use. When the dropper is angled with the tip 131 point downward, drops migrate to the lowest point on the ball before precise release downward to the eye E.

With reference to FIGS. 7 and 8, the use and operation of the preferred embodiment of the dropper 10 of the present invention is described. After removing the cap 12 from the housing 20 of the dropper 10, the reservoir 40 of the dropper 10 is lightly rested adjacent the cheek of the person below the person's eye E. The housing 20 of the dropper 10 is then rotated toward the person's eye E until the apogee 68 of the shoulder 60 of the dropper 10 rests lightly against the outer surface of the person's lower eyelid L. With the apogee 68 of the shoulder 60 continuing to engage the person's lower eyelid L, the entire dropper 10 is drawn slightly downward. The person can place a finger between the reservoir and the lower eyelid L and retract the lower eyelid L to create a pocket to receive dispensed drops D of medicinal liquid. In this position, the reservoir 40 and the shoulder 60 also cooperate to act as a safety guard to prevent the tip 31 of the dropper 10 from inadvertently touching the person's eye E while the dropper 10 is in use.

With the dropper 10 resting adjacent the person's cheek, the resilient cylindrical side walls 42 of the reservoir 40 are manually squeezed inwardly by the person (as shown by the Arrows C in FIGS. 7 and 8). The volume of the reservoir 40 is thereby decreased, creating a corresponding increase in pressure in the reservoir 40. The increased pressure causes medicinal fluid within the reservoir 40 to simultaneously flow (Arrows A and B) into both the intake 34 of the delivery tube 30 and the entry 82 of the annulus 80.

Squeezing the reservoir 40 causes sufficient movement of the delivery tube 30 to ensure any inadvertently trapped air pockets to dislodge and exit the delivery tube 30 before the first droplet D is formed. Prior elimination of the trapped air pockets within the delivery tube 30 prevents the medicinal liquid from being bubbled out into a person's eye E, and instead, allows the medicinal liquid to discharge as uniform droplets D.

Once the fluid exits the opening 32 in the tip 31 of the delivery tube 30 to form a droplet D (FIG. 7), the droplet D will release from the tip 31 to fall toward and land within the pocket formed by the retraction of the lower lid L of the person's eye E (FIG. 8). A person continues to squeeze the reservoir 40 of the dropper 10 to instill the prescribed number of eye drops D. Once the appropriate number of eye drops D have been instilled, the shoulder 60 of the dropper 10 may be rotated away from the person's lower eyelid L. The dropper 10 is then removed from the person's cheek to allow the cap 12 to be threaded back over the tip 31 of the dropper 10 onto the housing 20.

With particular reference to FIGS. 1 and 2, the use and operation of the most preferred embodiment of the dropper 110 of the present invention is described. As with the preferred embodiment of the dropper 10 of the present invention, the most preferred embodiment of the dropper 110 of the present invention is actuated by manually squeezing the sidewalls 42 of the reservoir 40 of the dropper 110. However, the medicinal liquid is only able to flow into the entry 88 of the annulus 80, to rise up the supply conduit 15 to exit out the outlet 84 of the annulus 80. As the liquid exits the annular outlet 84, the liquid will tend to wettably adhere to the exterior wall 135 of the rod 130 and flow toward the ball 137 at the tip 131 of the rod 130. The discharged liquid will continue to flow along the under belly 139 of the ball 137 where it will form a droplet D at the lowest point of the underbelly 139 of the ball 137. Once the droplet D is of sufficient mass, the droplet D will release from the ball 137 to fall toward the well formed within the lower lid L of the person's eye E (FIG. 1).

This disclosure is provided to reveal a preferred embodiment of the invention and a best mode for practicing the invention. Having thus described the invention in this way, it should be apparent that various different modifications can be made to the preferred embodiment without departing from the scope and fair meaning of this disclosure.

What is claimed is:

1. A liquid dropper comprising in combination:

a reservoir for holding a liquid to be discharged from the dropper;

said reservoir having an upper end located above a base;

said reservoir having a center line extending through said base and said upper end;

an opening located above said upper end of said reservoir when said dropper is oriented for release of liquid therefrom, said opening aligned with a central axis non-parallel to said center line of said reservoir;

a conduit extending from said opening to an inlet port located within said reservoir;

wherein said conduit includes a hollow outer casing having an elongate rod enshrouded within an inner surface of said casing;

said rod extending from a tip adjacent a nose of said casing to terminate at a low end adjacent a shoe of said casing; and said casing and said rod forming in combination an elongate hollow annulus, said annulus having an entry adjacent said said shoe of said casing and an outlet adjacent said nose of said casing.

2. The dropper of claim 1 wherein said rod is of sufficient length to extend slightly beyond a nose of said casing, such that droplets of liquid tend to form on said tip and fall toward a user's eye.

3. The dropper of claim 2 wherein said tip of said rod includes a ball attached to said tip, such that droplets of liquid tend to form along an underbelly of said ball prior to release from said tip of said rod.

4. A liquid dropper comprising in combination:

a reservoir for holding a liquid to be discharged from the dropper;

said reservoir having an upper end located above a base;

said reservoir having a center line extending through said base and said upper end;

an opening located above said upper end of said reservoir when said dropper is oriented for release of liquid therefrom, said opening aligned with a central axis non-parallel to said center line of said reservoir;

a conduit extending from said opening to an inlet port located within said reservoir;

wherein said conduit includes a hollow outer casing having an elongate tube enshrouded within an inner surface of said casing;

said tube extending from a tip adjacent a nose of said casing to terminate at a low end adjacent a shoe of said casing;

wherein said tip of said tube includes an orifice through which liquid may be discharged to fall toward the eye of a user; and wherein said low end of said tube includes an intake through which liquid may enter said tube to flow through said tube toward said orifice.

5. The dropper of claim 4 wherein said tip of said tube extends slightly beyond said nose of said casing, such that a drop forming at an end of said tip may drop from said tip to fall toward a user's eye.

6. The dropper of claim 5 wherein said low end of said tube extends beyond said shoe of said casing.

7. A liquid dropper comprising in combination:

a reservoir for holding a liquid to be discharged from the dropper;

said reservoir having an upper end located above a base;

said reservoir having a center line extending through said base and said upper end;

an opening located above said upper end of said reservoir when said dropper is oriented for release of liquid therefrom, said opening aligned with a central axis non-parallel to said center line of said reservoir;

a conduit extending from said opening to an inlet port located within said reservoir;

wherein said opening is located at a tip of an extension, said extension attached to said reservoir and oriented symmetrically about said central axis, said central axis intersecting said center line with said opening located in front of said center line;

wherein an interior angle between said central axis and said center line and located beneath said extension measures between 60° and 120°;

wherein said opening is located a distance from said center line of said reservoir similar to a distance said side wall is located spaced away from said center line of said reservoir; and wherein a shoulder is located between said extension and said reservoir, said shoulder having an oval perimeter with a major axis of the oval substantially parallel to said central axis and an apogee defining a portion of said shoulder most distant from said center line of said reservoir, said apogee extending away from said center line at least as far as said opening is from said center line, such that said shoulder can assist a user in keeping the opening of the extension from contacting the user's eye when the liquid dropper is utilized to dispense eye medication in an upright manner.

8. A method for manually delivering drops of liquid from a reservoir while holding the reservoir upright, the method including the steps of:

providing the reservoir with an upper end located over a base with the reservoir having a center line extending through the base and the upper end;

locating an opening above the base of the reservoir;

spacing the opening laterally away from the center line of the reservoir;

extending a conduit from the opening into the reservoir;

applying pressure to liquid in the reservoir, the pressure sufficient to cause liquid to rise up the conduit and exit the opening; and providing a shoulder between the opening and the reservoir, the shoulder extending away from the center line and beneath the opening a distance away from the center line at least as great as a distance that the opening extends away from the center line.

9. An eye medication dropper for discharge of liquid eye medication by persons who have difficulty tilting the head back and who have difficultly lifting the dropper above their eye being medicated, the dropper comprising in combination:

a liquid medication reservoir having a deformable side wall and a base below upper end;

said reservoir having a center line extending between said base and said upper end;

an opening located above said reservoir and spaced laterally away from said center line of said reservoir;

a conduit extending from an inlet port located within said reservoir to said opening, said conduit sufficiently constricted to allow the person to squeeze said side wall of said reservoir and control release of drops from said opening while said reservoir is oriented below said opening; and wherein said conduit includes an inner rod extending along at least a portion of an interior thereof, such that said conduit has an interior with a somewhat annular cross-section.

* * * * *